Figure 1:
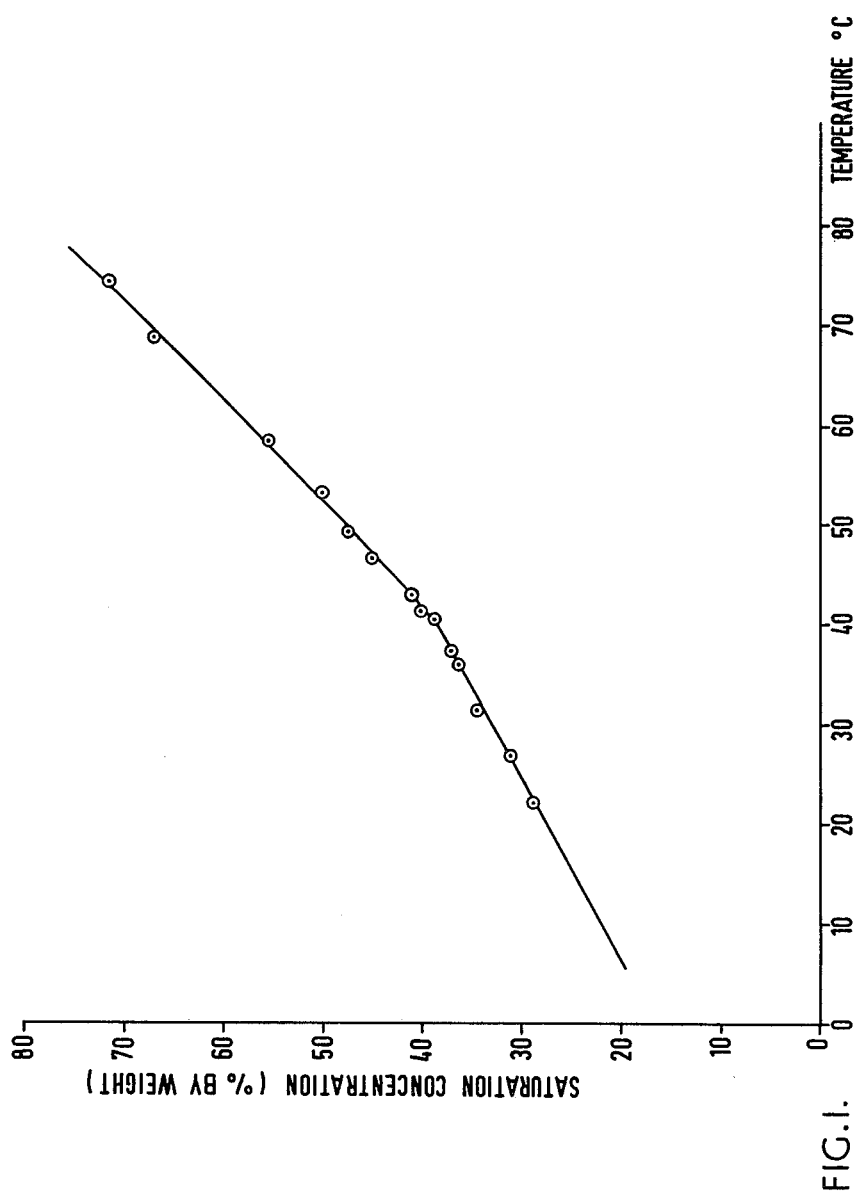

United States Patent [19]

Jenner et al.

[11] 4,343,934
[45] Aug. 10, 1982

[54] CRYSTALLINE 4,1',6'-TRICHLORO-4,1',6'-TRIDEOXY-GALACTOSUCROSE

[75] Inventors: Michael R. Jenner, Pangbourne; David Waite, Reading, both of England

[73] Assignee: Talres Development (N.A.) N.V., Netherlands Antilles

[21] Appl. No.: 212,897

[22] Filed: Dec. 4, 1980

[30] Foreign Application Priority Data

Dec. 18, 1979 [GB] United Kingdom ................ 7943495
Jul. 21, 1980 [GB] United Kingdom ................ 8023819

[51] Int. Cl.$^3$ .......................... C07H 3/04; C07H 5/02
[52] U.S. Cl. .................................. 536/122; 426/658; 426/548
[58] Field of Search ................ 426/548, 658; 536/122

[56] References Cited

FOREIGN PATENT DOCUMENTS 1543167 3/1979 United Kingdom .

OTHER PUBLICATIONS

Lee et al., Structural Functions of Taste in the Sugar Series: Binding Characteristics of Disaccharides, *J. Sci. Fd. Agric.* 1975,26 15137521.
Kirk–Othmer Encyclopedia of Chemical Technology, 3rd Ed., 1979, vol. 7, John Wiley & Sons: New York, pp. 243–285.
Hough, Selective Replacement of Hydroxyl Groups in Sucrose, Abstract 55, American Chemical Society Division of Carbohydrate Chemistry 172nd ACS National Meeting, San Francisco, Ca., Aug. 30–Sep. 2, 1976.

*Primary Examiner*—Joseph M. Golian
*Attorney, Agent, or Firm*—Ostrolenk, Faber, Gerb & Soffen

[57] ABSTRACT

Crystalline 4,1',6'-trichloro-4,1',6'-trideoxy-galactosucrose exists as the orthorhombic anhydrous form and as the pentahydrate, both of which are more stable than amorphous TGS. Crystals are obtained from seeded aqueous solutions, above 38° C. for the anhydrate; below 38° C. for the pentahydrate.

7 Claims, 3 Drawing Figures

CRYSTALLINE 4,1',6'-TRICHLORO-4,1',6'-TRIDEOXY-GALACTOSUCROSE

This invention relates to the carbohydrate sweetener 4,1',6'-trichloro-4,1',6'-trideoxygalactosucrose in a new form.

4,1',6'-Trichloro-4,1',6'-trideoxygalactosucrose, otherwise more properly known as 1,6-dichloro-1,6-dideoxy-β-D-fructofuranosyl 4-chloro-4-deoxy-α-D-galactopyranoside, and hereinafter referred to as TGS, is a potent sweetening agent. Its use and compositions containing it are described and claimed in British Pat. No. 1,543,167. The compound itself was first reported by Fairclough, Hough and Richardson, Carbohydrate Research 40(1975) 285-298, where it is described as syrup; but no sweet properties were ascribed to it. The substance is obtainable by a reaction sequence in which sucrose is tritylated in positions 6,1' and 6', and acetylated in the remaining five positions. The trityl groups are then removed with concurrent migration of the acetyl group on the 4-hydroxy group to the 6-hydroxy group. The resulting 4,1',6'-triol pentaacetate is then chlorinated using sulphuryl chloride and de-acetylated to give TGS. The product obtained in this way is a glass which is hygroscopic and which can be freeze-dried from an aqueous solution to give the glass as a fluffy white powder containing about 4% by weight of water. The hygroscopic nature of this form of TGS means that it must be kept in tightly sealed containers to prevent it degenerating into a sticky mass under humid conditions. Naturally, this property renders TGS glass difficult to use commercially and domestically, because of caking and so on. TGS has been prepared for several years, but up till now it has not been possible to overcome this problem.

We have now found that crystalline forms of TGS can be prepared which appear to be distinctly less hygroscopic than the glassy form.

Crystallisation was first achieved by seeding a concentrated aqueous solution of TGS (10 g in 5 ml) with an isomorphous crystalline substance which had been obtained by ion exchange resin treatment of an aqueous TGS solution. The solution had been treated with a mixture of Amberlite (Trade Mark) IRA 35 and IRC 72 (weak anion and cation exchange resins), in order to remove sodium and chloride ions. A fraction containing TGS as a syrup was obtained from the aqueous phase. A later fraction was obtained by elution of the resin with methanol and this material crystallised. A seed of this non-sweet, crystalline substance was used to seed a concentrated aqueous TGS solution. The exact nature of the non-sweet crystalline substance is not known to use, but it is possibly an anhydro-sugar derived from TGS. All subsequent crystallisations were effected using crystalline TGS itself as seed.

The product obtained by crystallisation from water at room temperature over several hours was a clear crystalline form of TGS, m.p. 36.5° C., containing about 20% by weight of water (approximately 5.5 moles of water per mole). Crystallisation of the glass from water at 60° C. gave a second clear crystalline form which was substantially anhydrous, containing 0.3-0.4% by weight of water, (approximately 0.07 to 0.09 moles of water per mole), m.p. 130° C. Crystallisation of the glass from undried methanol at 20° C. gave another form, again as clear crystals, m.p. 120° C., containing 2.3% by weight of water (approximately 0.5 mole of water per mole) and approximately 0.4% methanol.

A curve of solubility against temperature for TGS in water is shown in the accompanying drawings as FIG. 1. A single discontinuity in the curve at about 38° C. suggests the presence of effectively only two forms of TGS obtainable by crystallisation from water. Our findings are that these are the pentahydrate, obtained by crystallisation at temperatures below about 38° C., and the anhydrous form, obtained by crystallisation at temperatures above about 38° C., preferably above 60° C., e.g. about 70°-80° C. The pentahydrate can be dried in vacuo to remove some of its water of crystallisation to give various lower hydrates, but these appear only to consist of the pentahydrate structure with some water removed, rather than independent forms in their own right.

Thus, according to the present invention, there is provided crystalline 4,1',6'-trichloro-4,1',6'-trideoxygalactosucrose, especially crystalline anhydrous 4,1',6'-trichloro-4,1',6'-trideoxygalactosucrose, and also its crystalline pentahydrate, i.e. 4,1',6'-trichloro-4,1',6'-trideoxygalactosucrose pentahydrate, ($C_{12}H_{19}O_8Cl_3$.5-$H_2O$). There is also provided a method of preparing crystalline 4,1',6'-trichloro-4,1',6'-trideoxygalactosucrose by cooling a seeded saturated aqueous solution of 4,1',6'-trichloro-4,1',6'-trideoxygalactosucrose and collecting the crystallised material.

Figure 2:
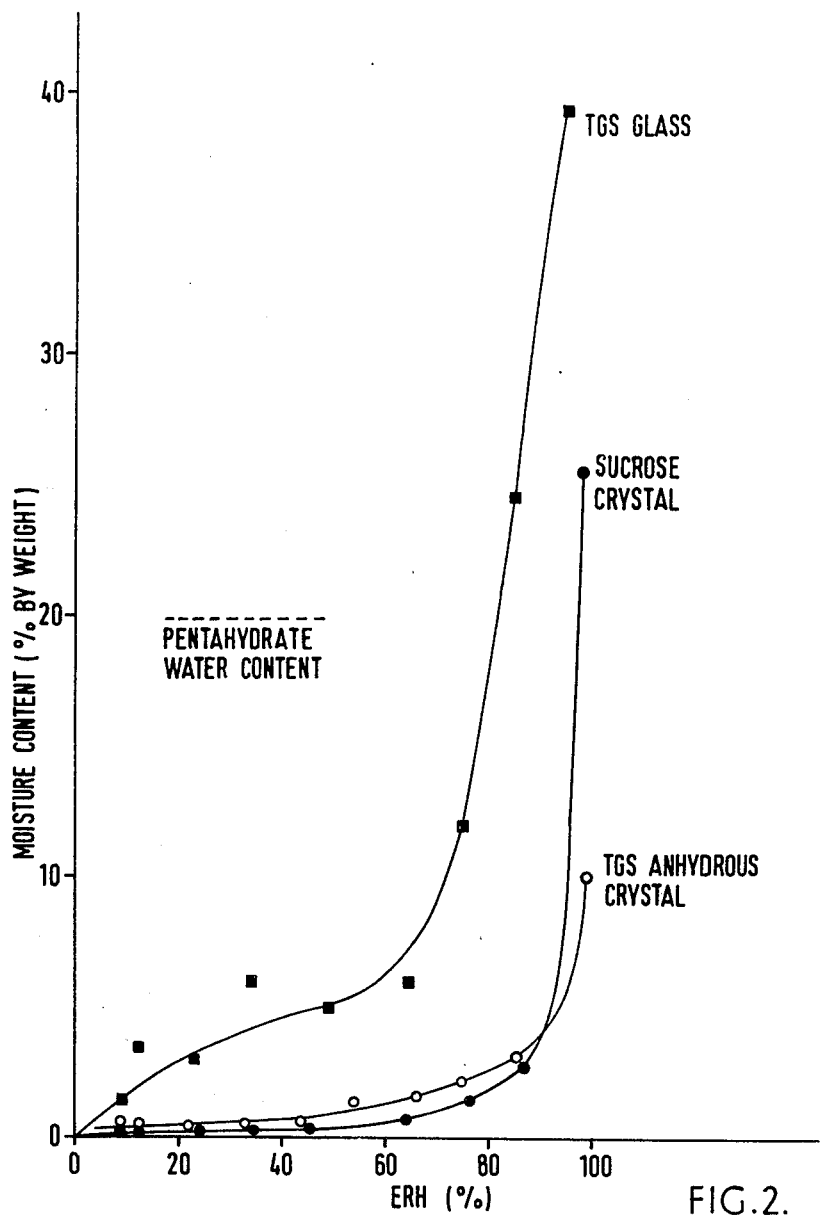

The compounds according to the present invention possess the same degree of sweetness as TGS in glass form and have the additional advantage of being considerably less hygroscopic, thus permitting easier handling and formulation. The anhydrous form, particularly, is very stable under humid conditions. Sorption isotherms for the anhydrous crystalline form and the glass show that the moisture adsorbed by the crystalline form is very much less than that adsorbed by the glass, which rapidly deliquesces at high humidities. The anhydrous crystalline form is, in fact, remarkably similar to crystalline sucrose in its adsorption characteristics as may be seen from FIG. 2 of the accompanying drawings which represents a plot of water content against ERH (equilibrium relative humidity) at 21° C., using a NOVA-SINA equi-HYDROSCOPE humidity measuring instrument for the crystalline anhydrous form of TGS, sucrose and TGS glass (ascending curves). The close similarity of TGS anhydrate to sucrose is readily apparent, while the glass is extremely hygroscopic, especially at a humidity over 70%. No comparative curve for the pentahydrate could be obtained as the substance lost water at low humidity and rapidly deliquesced at higher humidities, thus rendering measurement impossible.

Figure 3:
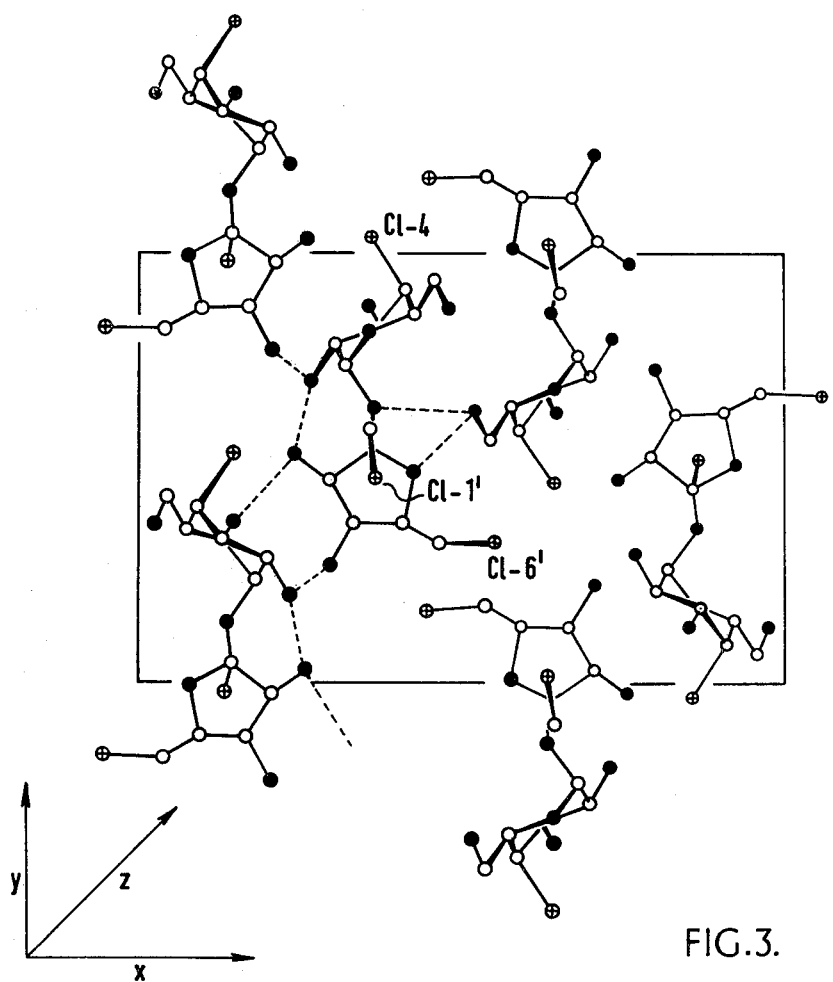

The anhydrous crystalline form has a pleasing orthorhombic, needle-like crystal structure. FIG. 3 in the accompanying drawings is a representation of the unit cell, based on X-ray crystallographic data. The structure does not contain any suitable sites for water, and any small amounts of water in the substance are probably adsorbed on the surfaces of the crystals.

The following table contains the positional parameters (atomic coordinates) which were derived by X-ray crystallography on anhydrous crystalline TGS.

TABLE

| ATOM | Atomic co-ordinates ($\times 10^4$) with estimated standard deviations in parentheses | | |
|---|---|---|---|
| | x | y | z |
| C-1 | 3183(3) | 7374(5) | 1797(9) |

TABLE-continued

| ATOM | Atomic co-ordinates (× 10⁴) with estimated standard deviations in parentheses | | |
|---|---|---|---|
| | x | y | z |
| C-2 | 3020(4) | 7831(5) | 3692(9) |
| C-3 | 3718(4) | 8265(5) | 4581(9) |
| C-4 | 4106(3) | 9097(5) | 3345(10) |
| C-5 | 4236(4) | 8566(5) | 1481(10) |
| C-6 | 4575(4) | 9337(6) | 83(10) |
| O-1 | 3635(2) | 6403(3) | 2060(6) |
| O-2 | 2683(3) | 7034(4) | 4839(8) |
| O-3 | 3543(3) | 8701(4) | 6333(7) |
| Cl-4 | 3561(1) | 10338(1) | 3106(3) |
| O-5 | 3552(2) | 8166(3) | 712(6) |
| O-6 | 4782(3) | 8691(4) | −1490(7) |
| C-1' | 3567(4) | 5937(5) | −1160(9) |
| C-2' | 3569(4) | 5510(5) | 827(9) |
| C-3' | 2929(3) | 4700(5) | 1311(9) |
| C-4' | 3300(4) | 3741(5) | 2262(10) |
| C-5' | 4078(4) | 3745(5) | 1470(10) |
| O-2' | 4236(2) | 4905(3) | 1152(7) |
| O-3' | 2407(3) | 5277(4) | 2410(8) |
| O-4' | 2960(3) | 2700(4) | 1939(8) |
| C-6' | 4626(4) | 3242(6) | 2788(11) |
| Cl-1' | 3643(1) | 4812(2) | −2727(3) |
| Cl-6' | 5548(1) | 3304(2) | 1922(3) |

The crystal data are as follows:

Orthorhombic; space group $P2_12_12_1$ (See International Tables For X-Ray Crystallography, Kynoch Press, 1965);

$$a = 18.21(1), b = 7.36(1), c = 12.04(1)Å;$$

The slope of the solubility curve, FIG. 1, shows that in the temperature range needed for formation of the anhydrous crystals, i.e. above about 38° C., the degree of recovery of TGS in a recrystallisation is very good. Thus, for example, a saturated solution at 75° C. has a solids content of about 73% while at 40° C. the saturated solids content is about 39%. To take a concrete example, a 100 g sample of a saturated solution at 75° C. contains 27 g of water and 73 g of TGS. When this sample is cooled to 40° C., 27 g of water remain, but in a solution with a solids content of 39% and a water content of 61%. The solution thus contains 17.26 g TGS, 55.74 g of TGS having precipitated a yield of 76.35%. TGS can thus be crystallised in good yield from a sample water crystallisation above 40° C.

Alternatively, the pentahydrate may be obtained by crystallisation from water below 38° C. For example, by extrapolation from FIG. 1, a saturated solution at 35° C. contains about 36% TGS, while at 10° C. the content is only about 16% TGS, so a crystallisation will yield about 66% of TGS as the crystalline pentahydrate.

Both the anhydrous and the pentahydrate crystalline forms of TGS possess the same degree of sweetness as the glassy form. Thus, for example, taste panels have indicated that TGS is several hundred times sweeter than sucrose. The exact figure depends on the concentration of the sucrose solution with which a TGS solution is compared for equal sweetness. The following figures are typical:

| concentration of sucrose | sweetness factor for TGS |
|---|---|
| 4% | 667 |
| 7% | 500 |
| 10% | 450 |

The crystalline TGS can thus be used to sweeten all types of substances, including ingestible compositions (i.e. intended for consumption) and oral compositions (i.e. intended for oral application without swallowing, e.g. mouthwashes). It can be formulated, in particular, as a solid composition in association with a comestible carrier, diluent or excipient (.e.g. in sweetening tablets etc) or with a foodstuff or beverage concentrate (e.g. a dry formulation for dilution with water to form a foodstuff, confection or beverage).

The following examples illustrate the invention further. All temperatures are in °Celsius; Amberlite is registered Trade Mark:

EXAMPLE 1

TGS was obtained by the method of Fairclough et al. (op. cit.) A batch of 50 g dissolved in hot acetone was chromatographed on a column of silica gel (600 g), by elution with dichloromethane (1 liter) and gradient elution with dichloromethane/acetone (20 liters in all) to obtain a product showing only 1 spot on thin layer chromatography. A further batch of 60 g was treated similarly, and a total of 90 g was obtained by combining the two yields. This material was dissolved in water (10% concentration) and treated with about 100 g of a 50:50 mixture of Amberlite IRA 35 and IRC 72 resins for 1 hour with stirring. The solution was filtered and concentrated to yield TGS (about 33 g). The resin was then eluted with methanol (4×500 ml) and the methanol concentrated to yield 55 g of a non-sweet material which crystallised. A small sample of this material was subsequently added as a seed to a saturated aqueous solution of TGS at about 30°. The solution was cooled and crystalline TGS was filtered off. The crystals were found to be of TGS pentahydrate, mp 36.5°. The unknown crystals were thus apparently isomorphous with TGS.

One or two of the TGS pentahydrate crystals were used to seed a hot saturated aqueous solution of TGS (about 60°) and this, on cooling, gave crystalline anhydrous TGS, m.p 130°.

EXAMPLE 2

TGS pentaacetate (2.1 kg) obtained by the method of Fairclough et al. (op. cit) was deacetylated by treatment with methanolic sodium methoxide to give TGS as a syrup (ca. 1360 g) which was dissolved in water (ca.10%) and filtered through charcoal. The filtrate was concentrated to a syrup and redissolved in water at about 65% by weight. The solution was heated and seeded at about 65°–70° with an authentic sample of crystalline TGS (anhydrous). The solution was cooled to 40° and then further to about ambient temperature. The crystalline material precipitated was filtered off.

A yield of 710 g was obtained. The mother liquors were heated, concentrated reseeded and cooled to yield a further 255 g. A third crystallisation gave a further 77.5 g, providing a total yield of 1042.5 g (76.6%) of pure TGS as anhydrous crystals mp 130°, having the X-ray crystallographic parameters cited above.

We claim:

1. Crystalline 4,1',6'-trichloro-4,1',6'-trideoxygalactosucrose.

2. Crystalline substantially anhydrous 4,1',6'-trichloro-4,1',6'-trideoxygalactosucrose.

3. Crystalline 4,1',6'-trichloro-4,1',6'-trideoxygalactosucrose pentahydrate of mp about 36.5° C.

4. A method of preparing crystalline 4,1',6'-trichloro-4,1',6'-trideoxygalactosucrose by cooling a seeded saturated aqueous solution of 4,1',6'-trichloro-4,1',6'-trideoxygalactosucrose and collecting the crystallised material wherein the seed is selected from the group consisting of (a) crystalline 4,1',6'-trichloro-4,1',6'-trideoxygalactosucrose and (b) a non-sweet crystalline substance which is isomorphous with 4,1',6'-trichloro-4,1',6'-trideoxygalactosucrose recoverable by methanol elution of a 4,1',6'-trichloro-4,1',6'-trideoxygalactosucrose obtained by ion exchange treatment of an aqueous 4,1',6'-trichloro-4,1',6'-trideoxygalactosucrose solution.

5. A method according to claim 4, effected above about 38° C.

6. A method according to claim 4, in which the solution is one which is saturated at above 60° C.

7. A method according to claim 4, effected below about 38° C.

* * * * *